United States Patent
Lin et al.

(10) Patent No.: US 7,223,503 B2
(45) Date of Patent: May 29, 2007

(54) METHOD FOR REPAIRING OPAQUE DEFECTS ON SEMICONDUCTOR MASK RETICLES

(75) Inventors: Wei-Lian Lin, Hsinchu (TW);
Chian-Hun Lai, Taichung (TW);
Shao-Chi Wei, Taichung (TW);
Chi-Kang Chang, Rueitang Township, Taipei County (TW); Chia-Hsien Chen, Puli town, Nan-Tou County (TW);
Shan-Chan Sue, Toufen Township, Miaoli County (TW); Chun-Hung Kung, Hsinchu (TW)

(73) Assignee: Taiwan Semiconductor Manufacturing Company, Hsin-Chu (TW)

( * ) Notice: Subject to any disclaimer, the term of this patent is extended or adjusted under 35 U.S.C. 154(b) by 521 days.

(21) Appl. No.: 10/748,075

(22) Filed: Dec. 30, 2003

(65) Prior Publication Data
US 2005/0146715 A1    Jul. 7, 2005

(51) Int. Cl.
*G03F 1/00*    (2006.01)
(52) U.S. Cl. ............. 430/5; 356/433; 356/448
(58) Field of Classification Search ............. None
See application file for complete search history.

(56) References Cited

U.S. PATENT DOCUMENTS

| | | | |
|---|---|---|---|
| 5,291,269 A * | 3/1994 | Ledger ............. | 356/504 |
| 5,744,381 A * | 4/1998 | Tabata et al. ....... | 356/237.5 |
| 5,804,813 A * | 9/1998 | Wang et al. ........ | 250/201.3 |
| 6,322,935 B1 * | 11/2001 | Smith ............... | 250/307 |
| 6,444,971 B1 * | 9/2002 | Engelhardt et al. .... | 356/445 |
| 6,593,040 B2 * | 7/2003 | Smith ............... | 430/5 |
| 6,651,226 B2 * | 11/2003 | Houge et al. ......... | 716/4 |
| 6,891,629 B2 * | 5/2005 | Jackson ............. | 356/630 |

* cited by examiner

*Primary Examiner*—Gregory J. Toatley, Jr.
*Assistant Examiner*—Juan D. Valentin, II
(74) *Attorney, Agent, or Firm*—Duane Morris LLP

(57) ABSTRACT

A method is disclosed for repairing an opaque defect on a mask substrate. After examining one or more opaque patterns in a predetermined area of the mask substrate, at least one opaque defect in the opaque patterns is identified based on a difference between its light reflection rate and a reference reflection rate. A residue height of the opaque defect is further determined based on its light transmission rate, and a repair formula such as an etching dosage is devised based on the determined residue height.

20 Claims, 3 Drawing Sheets

METHOD FOR REPAIRING OPAQUE DEFECTS ON SEMICONDUCTOR MASK RETICLES

BACKGROUND

The present disclosure relates generally to semiconductor device manufacturing, and more particularly to a method and system for repairing photolithography mask reticles used in the component and circuit patterning processes of a semiconductor device substrate.

The manufacture of semiconductor integrated circuits (ICs) and devices require the use of many photolithography process steps to define and create specific circuit components and circuit layouts onto an underlying substrate. Conventional photolithography systems project specific circuit and/or component images, defined by a mask pattern reticle, onto a flat substrate coated with a light sensitive film (photoresist) coating. After image exposure, the film is then developed leaving the printed image of the circuit and/or component on the substrate. The imaged substrate is subsequently processed with techniques such as etching and doping to alter the substrate with the transferred pattern.

It is critical to the yields of the photolithography operations and to the product yields that the mask reticles are free of defects and damage that may be transferred as undesired patterns and images upon the product substrate.

Advanced semiconductor manufacturing operations utilize mask reticle defect inspection systems to help identify and measure the mask reticle defects and damage. In addition, mask reticle repair systems incorporating focused ion beams (FIBs), are usually used to repair the mask reticles such that the reticles can again, become usable for production operations. The use of these mask reticle inspection and repair systems upon new and in-production mask reticles save the manufacturing operations significant costs related to poor process and device yields, as well as costs related to having new mask reticles fabricated and qualified for production usage.

Mask reticle defects manifest largely by two major forms. Transparent defects are light-passing defects that are located upon regions of the mask reticles where opaque material should be located. The conventional repair method for transparent defects is via the use of a programmed FIB, usually a carbon-rich or metallic ion beam of low keV energy, to deposit an adherent opaque film onto the identified repair regions of the mask reticle. Opaque defects are light-blocking defects that are located upon regions of the mask reticles where such material should be absent. The conventional repair method for opaque defects is via the use of a programmed FIB, usually a Gallium ion beam of between 30 to 75 kilo-electron volts (keV) energy, to etch or sputter the identified defect off of the mask reticle.

Ideally, opaque defect removal must be performed with some precision as to not over-etch and induce new damage to the mask substrate material (typically quartz) located under the removed defect. Such mask substrate damage may itself, be manifested as a new mask reticle defects and damage that may be transferred as undesired patterns and images upon the product substrate. The FIB etching dosage (or etch quantity) must be sufficient enough to clear and remove the entire height and volume of the opaque defect region without inducing significant damage to the underlying mask substrate. Many semiconductor manufacturing operations may choose to maintain a relatively high, fixed FIB etching dosage to ensure complete removal of the opaque defects. The conventional method counts upon a net benefit gain from the removal of the opaque defect versus the possible creation of new mask defects.

Other semiconductor manufacturing operations choose to implement extra procedures to more precisely remove the opaque defects without inducing additional mask reticle defects. Additional procedures are implemented to measure the height of the opaque mask reticle defects in order for a precise FIB etch dose to be determined to remove the defect without damage to the mask substrate. Typical techniques used to measure height of the opaque defects include atomic force microscopy (AFM) and scanning electron microscopy (SEM). Such analytical techniques are capable of obtaining defect height measurements with the required nano-meter scale precision and accuracy.

However, such analytical procedures are not well-suited for an efficient manufacturing operation. These analytical tools and procedures require highly-trained operational expertise, typically an engineer or specialized technician instead of the standard manufacturing operator level expertise. These analytical tools themselves are expensive and slow to operate, requiring much dedicated capital expense as well as much focus and time to perform the required procedures. These translate to high costs associated for the measurement operations and for the time-related costs due to loss of production usage of the measured mask reticle.

What is desirable is an improved opaque defect removal method that can precisely remove the undesired defect without inducing any additional damage upon the mask reticle. The improved method is also desired to be easily incorporated into the manufacturing operations with minimal requirements for engineer and special expertise. Such method would also be of low operational costs as well as incurring minimal impact to the non-production service period of the mask reticles in the repair cycle.

SUMMARY

A method is disclosed for repairing an opaque defect on a mask substrate. After examining one or more opaque patterns in a predetermined area of the mask substrate, at least one opaque defect in the opaque patterns is identified based on a difference between its light reflection rate and a reference reflection rate. A residue height of the opaque defect is further determined based on its light transmission rate, and a repair formula such as an etching dosage is devised based on the determined residue height.

Various advantages of the disclosed method will become clearer with the illustrations below and provided claims.

DESCRIPTION

The present disclosure describes a method and system for low cost, efficient removal of opaque defects from semiconductor mask reticles while inducing minimal residual damage to the underlying mask substrate material. The disclosed method utilizes the conventional mask reticle defect inspection and mask repair FIB systems to accomplish the defect identification and removal operations. The disclosed method does not require the implementation and use of complex analytical tools such as the AFM and SEM to measure the height of the opaque defects. The method of the present disclosure features the use of the mask reticle defect identification inspection tool to obtain the light transmission and reflectivity characteristics of the identified opaque defects to determine their height and subsequently, the etch dose for the FIB mask reticle repair process.

Figure 1:
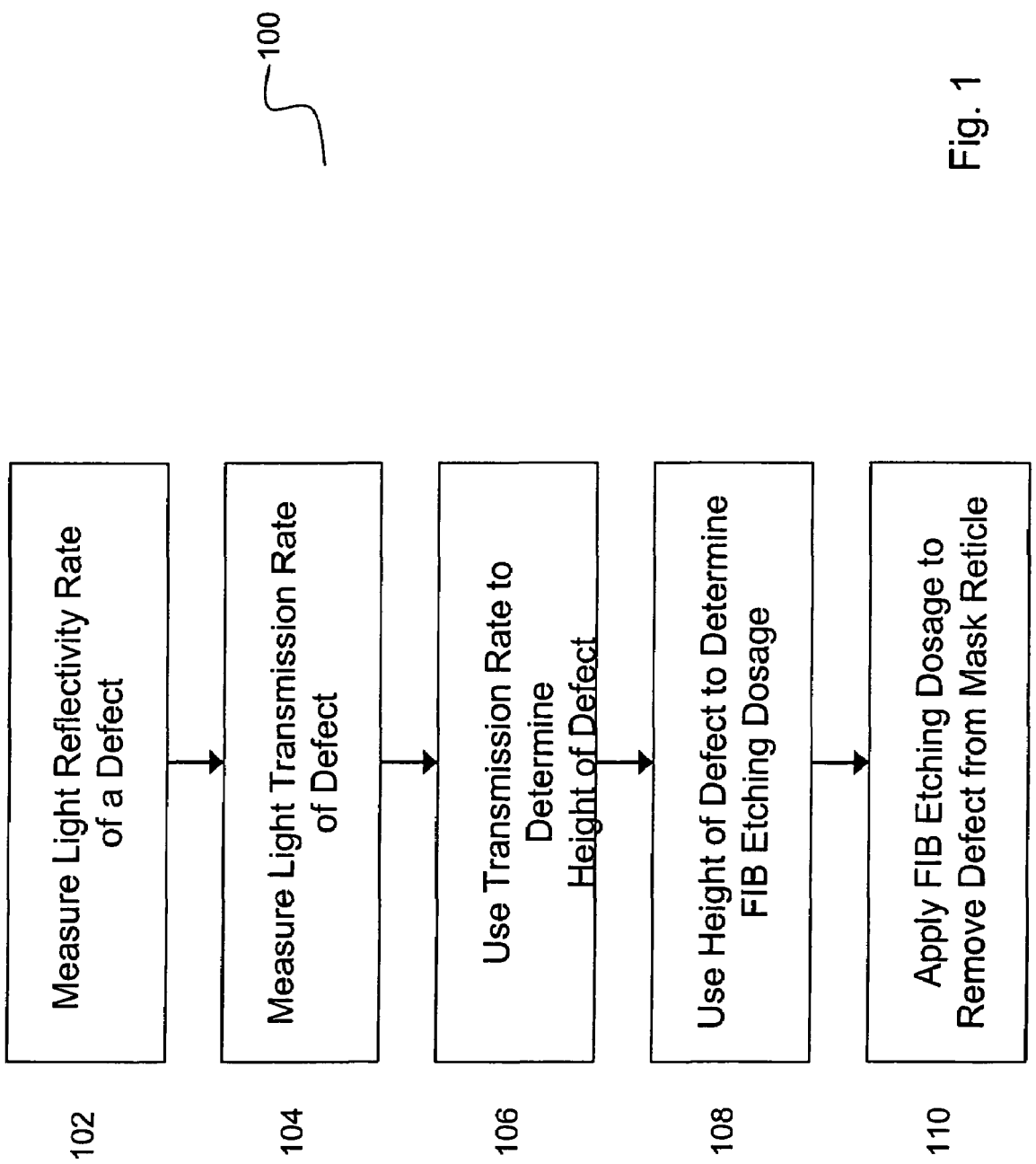
FIG. 1 is a flow diagram illustrating steps of an opaque defect repair method in accordance with one example of the present disclosure.

FIG. 1 is a flow diagram 100 illustrating process steps for an opaque defect repair method in accordance with one example of the present disclosure. The first two steps of the method utilize a mask reticle identification, inspection tool to obtain both qualitative and quantitative information concerning the identified opaque defects. The first step 102 measures the reflectivity percentage (R %) of light from the opaque defects using the mask reticle inspection system. This measurement utilizes the featured stable, constant intensity projected light of the inspection system to obtain the R % data for each identified opaque defect. The R % measurement from the opaque defect can be compared to the previously determined R % value for a full height opaque feature of a same size and shape on the mask reticle. If the R % of the opaque defect is less than the R % of the full height opaque feature, this indicates that the opaque defect is not of full height, requiring further procedures to determine an assigned FIB etch dose for precise removal of defect.

For example, typical mask reticles use Chromium (Cr) composite metal as the desired opaque material for mask patterns. The R % of a full height feature comprised of the Cr composite may be 25%, which is deemed as a reference reflection rate. This 25% light reflectivity level is used to establish the R % value for full height and fully opaque. Therefore, any opaque defect that has an R % value measured at less than the full height, fully opaque value, <25%, can be classified as an opaque defect with less than full height, requiring further procedures to determine an assigned FIB etch dose for precise removal of defect. By using the R % information of the opaque defects, qualitative judgment can be made concerning the FIB etch requirement for removal of the defects.

In the second step 104, the next measurement is performed utilizing the mask reticle identification, inspection tool to obtain the quantitative information concerning the identified opaque defects. This measurement utilizes again, the featured stable, constant intensity projected light of the inspection system to obtain light transmission information for each identified opaque defect. The measured percentage (T %) of light transmitted through the previously identified, non-full height opaque defect is used to determine the actual height of the defect (step 106).

The T % value for each opaque defect is correlated to a defect height table that has been previously determined and established. It is noted that the measured light transmission through a uniform opaque material of a fixed area size, is very predictable, repeatable with a near linear characteristic with respect to film height (or thickness). This characteristic allows for the quantitative calculation of the height of an opaque defect by using the T % information collected using the mask reticle inspection system.

Figure 2:
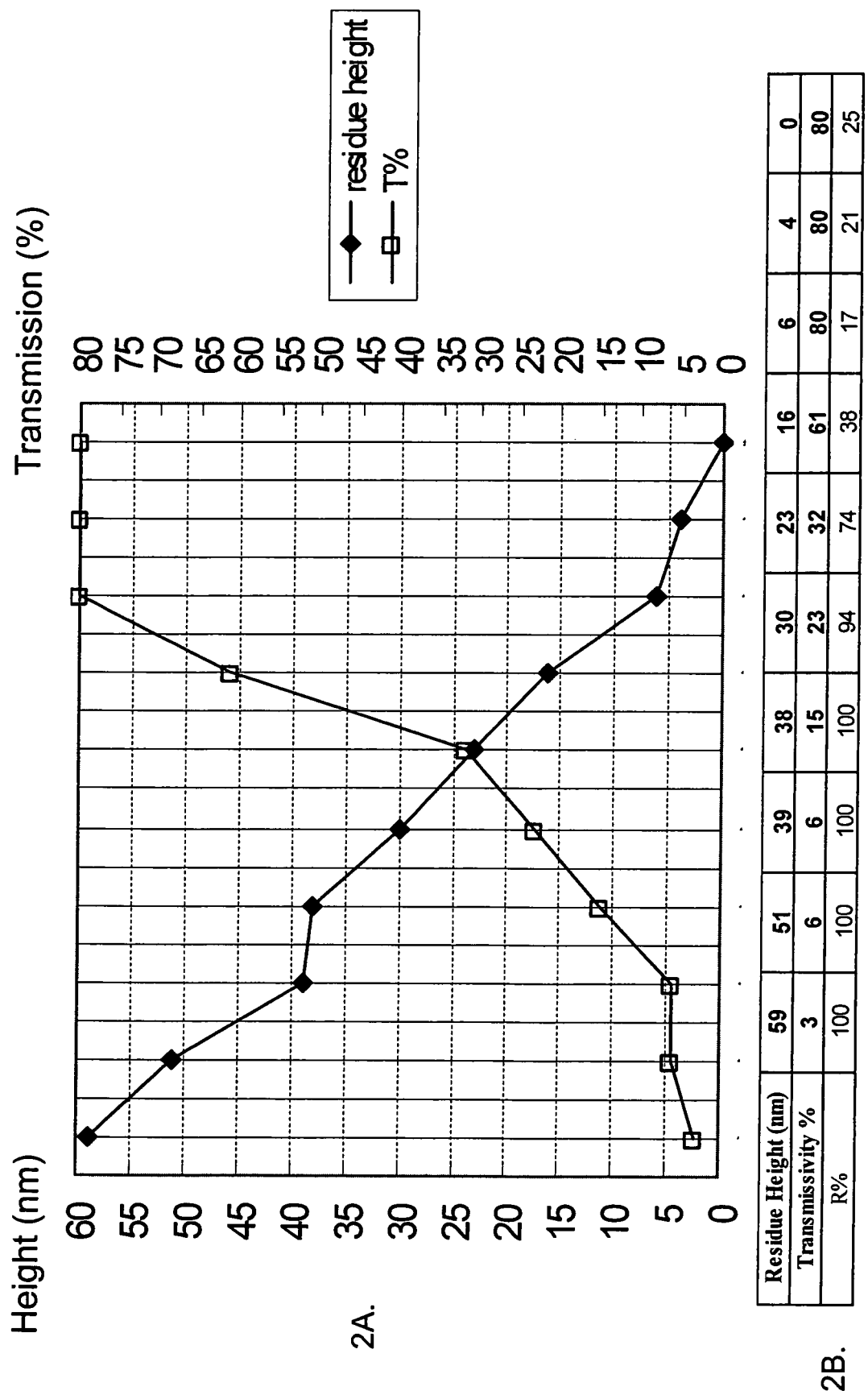
FIGS. 2A and 2B are a graph and data table that illustrates the relationship of light transmission to height of an opaque defect.

FIGS. 2A and 2B are a graph and the associated data table that illustrates the relationship of light transmission to the heights of opaque defects. FIG. 2A shows the near linear relationship of T % to the height of the opaque defect. FIG. 2B is a data table of the T % and defect height data used to generate the graphed curves of FIG. 2A. As an example, the graph and data table of FIGS. 2A and 2B show that for a defect with a measured T % of 20%, the calculated defect height is approximately 34 nanometers (nm). Similarly, the graph and table show that the T % value of 80% indicates that the opaque defect height is near zero, or non-existent.

Referring back to the flow diagram of FIG. 1, the fourth step 108 is the determination of the FIB etch dose used for removing the opaque defect. This step uses the calculated defect height as determined by the previous step 106 to assign a repair formula or repair dosage such as the FIB etching dosage for the mask reticle repair. This step effectively functions as the various steps used by the conventional mask reticle repair methodologies that utilize the AFM and SEM analytical tools for determining the height of the opaque defects one after another individually.

Figure 3:
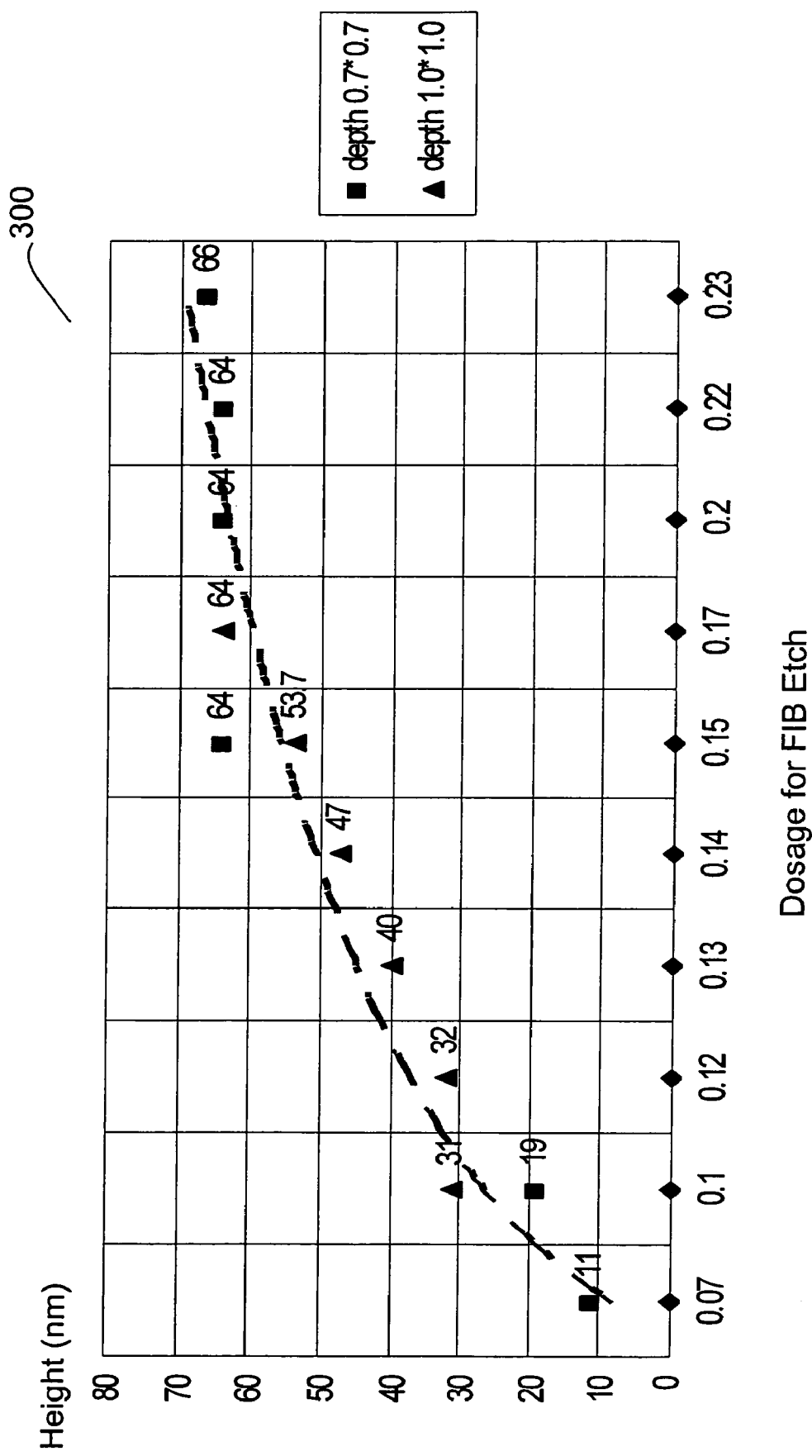
FIG. 3 is a graph that illustrates the relationship of required FIB etching dosage for removal of an opaque defect with a given height.

FIG. 3 is a graph 300 that illustrates the relationship of a typical FIB etch process to the defect heights detected used by FIB system such as model Micron 800. As an example, this graph assumes that contacts are used for illustration and each contact is has a size of 700 nm by 700 nm. The graph shows that an FIB etch dose of approximately 0.135 nC/UM$^2$ is the minimum required to etch/remove an opaque defect with a height of 48 nm. Using such previously established characterization data, the FIB etch dose for precise removal of opaque defects can be determined. The calculated FIB etching dosage for each identified opaque defect can now be applied to precisely remove the defects from the mask reticle with minimal defects and damage induced upon the mask, which is the last step 110 of the flow diagram 100 of FIG. 1. It is understood that standard repair methods for removing opaque defects can be used, for example, via the use of a programmed FIB, usually with a Gallium ion beam having more than 30 kilo-electron volts (keV) energy. It is further notices, when the term "etch" is used in this disclosure, a sputter method can equally be applied to remove the identified defect off of the mask reticle.

The opaque defect removal method utilized in accordance with the present disclosure is a low cost, efficient system for the precision removal of opaque defects while inducing minimal new defects and damage upon the mask reticles. The disclosed method does not require the time-consuming, expensive usage of specialized analytical tools such as the AFM and SEM. The method of the disclosure features the usage of a conventional tool, the mask reticle defect identification inspection system, to obtain reflection and transmission information, R % and T %, of the opaque defects. The additional defect information is then utilized in accordance with the disclosed method to determine the height of the defects and subsequently, the calculations of the required FIB etching dosage for precise removal of the same.

The method disclosed is suitable and compatible for implementation within existing, conventional and future photolithography mask reticle technologies. The defect data processing aspects of the disclosed method are well suited for implementation within factory automation and/or virtual specification systems such that process parameters defined within the mask repair operations are seamless and requiring little or no additional attention from the engineering and manufacturing personnel.

The above disclosure provides several examples for implementing the different features of the disclosure. Specific examples of components and processes are described to help clarify the disclosure. These are, of course, merely examples and are not intended to limit the scope of the disclosure from that described in the claims.

While the invention has been particularly shown and described with reference to the preferred embodiment thereof, it will be understood by those skilled in the art that various changes in form and detail may be made therein without departing from the spirit and scope of the invention, as set forth in the following claims.

What is claimed is:

1. A method for evaluating at least one opaque defect on a mask substrate, the method comprising:
    identifying an opaque defect based on a difference between its light reflection rate and a reference reflection rate;
    determining a residue height of the opaque defect based on a light transmission rate;
    devising a repair formula based on the determined residue height; and
    repairing the opaque defect according to the repair formula.

2. The method of claim 1 wherein the identifying further includes identifying the reference reflection rate by examining the light reflection rates of one or more normal opaque mask patterns.

3. The method of claim 1 wherein the identifying further includes imposing a light source over at least one predetermined pattern on the mask substrate and determining the light reflection rate thereof.

4. The method of claim 1 further comprising determining a co-relation between the light transmission rate and the residue height.

5. The method of claim 4 wherein the determining the residue height further includes:
    imposing a light source over the opaque defect and obtaining its light transmission rate; and
    identifying the residue height based on the light transmission rate and the co-relation with the residue height.

6. The method of claim 1 further comprising etching the opaque defect using the devised repair formula.

7. A method for repairing an opaque defect on a mask substrate, the method comprising:
    examining one or more opaque patterns in a predetermined area of the mask substrate;
    identifying at least one opaque defect in the opaque patterns based on a difference between its light reflection rate and a reference reflection rate;
    determining a residue height of the opaque defect based on its light transmission rate;
    devising a repair formula based on the determined residue height; and
    repairing the opaque defect according to the repair formula.

8. The method of claim 7 wherein the examining further includes:
    imposing a light source over the opaque patterns on the mask substrate;
    determining the light reflection rates thereof; and
    determining a reference reflection rate.

9. The method of claim 7 further comprising determining a co-relation between the light transmission rate and the residue height for devising the repair formula.

10. The method of claim 9 wherein the determining the residue height further includes:
    imposing a light source over the opaque defect and obtaining its light transmission rate; and
    identifying the residue height based on the light transmission rate and the co-relation.

11. The method of claim 7 further comprising removing the opaque defect according to the devised repair formula.

12. The method of claim 11 wherein the removing further includes removing the opaque defect using an ion beam.

13. The method of claim 12 wherein the ion beam has an energy between 30 to 75 keV.

14. A method for repairing an opaque defect on a mask substrate, the system comprising:
    examining one or more opaque patterns of the mask substrate;
    imposing a light source over the opaque patterns;
    determining light reflection rates of the opaque patterns;
    identifying one or more normal opaque patterns based on the determined light reflection rates;
    identifying a reference reflection rate based on the light reflection rates identified for the normal opaque patterns;
    identifying at least one opaque defect in the opaque patterns based on a difference between its light reflection rate and the reference reflection rate;
    determining a light transmission rate of the opaque defect;
    determining a residue height of the opaque defect based on its light transmission rate;
    devising a repair formula based on the determined residue height; and
    repairing the opaque defect according to the repair formula.

15. The method of claim 14 further comprising determining a co-relation between the light transmission rate and the residue height for devising the repair formula.

16. The method of claim 15 wherein the determining a light transmission rate of the opaque defect further includes:
    imposing an inspection light with a stable intensity over the opaque defect and measuring its light transmission rate; and
    identifying the residue height based on the light transmission rate and the co-relation.

17. The method of claim 15 wherein co-relation is a linear co-relation.

18. The method of claim 14 further comprising removing the opaque defect according to the devised repair formula.

19. The method of claim 18 wherein the removing further includes removing the opaque defect with a focused ion beam.

20. The method of claim 19 wherein the focused ion beam is a Gallium ion beam with an energy level above 30 keV.

* * * * *